(12) United States Patent
Hakkinen et al.

(10) Patent No.: US 7,501,135 B2
(45) Date of Patent: *Mar. 10, 2009

(54) GASTRIC ACID SECRETION

(75) Inventors: John Hakkinen, North Stonington, CT (US); Roelof Marthinus Horak, Pretoria (ZA); Vinesh Maharaj, Pretoria (ZA)

(73) Assignee: Conopco, Inc., Englewood Cliffs, NJ (US)

( * ) Notice: Subject to any disclaimer, the term of this patent is extended or adjusted under 35 U.S.C. 154(b) by 542 days.

This patent is subject to a terminal disclaimer.

(21) Appl. No.: 10/921,364

(22) Filed: Aug. 19, 2004

(65) Prior Publication Data

US 2005/0079233 A1    Apr. 14, 2005

Related U.S. Application Data

(60) Continuation of application No. 10/171,640, filed on Jun. 17, 2002, now Pat. No. 6,808,723, which is a division of application No. 09/691,582, filed on Oct. 18, 2000, now Pat. No. 6,488,967.

(30) Foreign Application Priority Data

Oct. 27, 1999    (GB) .................................. 9925457.5

(51) Int. Cl.
  *A61K 35/78* (2006.01)
(52) U.S. Cl. ...................................... 424/725; 514/925
(58) Field of Classification Search ........................ None
  See application file for complete search history.

(56) References Cited

U.S. PATENT DOCUMENTS

| | | | |
|---|---|---|---|
| 4,062,950 A | 12/1977 | Frommer et al. ............... 514/35 |
| PP4,199 P | 1/1978 | Cobia et al. |
| 4,130,714 A | 12/1978 | Sarges ..................... 548/301.1 |
| 4,174,439 A | 11/1979 | Rauenbusch et al. ........ 536/55.3 |
| 4,185,116 A | 1/1980 | Barnish et al. ............... 514/567 |
| 4,251,528 A | 2/1981 | Brittain et al. ........... 514/232.8 |
| 4,254,256 A | 3/1981 | Otani et al. ................. 536/17.2 |
| 4,302,447 A | 11/1981 | Horrobin ..................... 424/642 |
| 4,302,477 A | 11/1981 | Mendy et al. ................ 426/250 |
| 4,393,049 A | 7/1983 | Horrobin ..................... 424/643 |
| 4,436,745 A | 3/1984 | York, Jr. ..................... 514/389 |
| 4,438,272 A | 3/1984 | York, Jr. ................... 548/301.1 |
| 4,464,382 A | 8/1984 | Tanouchi et al. ............. 514/183 |
| 4,540,704 A | 9/1985 | Ueda et al. ................... 514/389 |
| 4,584,289 A | 4/1986 | Jarreau et al. ................ 514/182 |
| 4,600,724 A | 7/1986 | Sestanj et al. ................ 514/510 |
| 4,634,765 A | 1/1987 | Liu ........................... 536/17.4 |
| 4,639,436 A | 1/1987 | Junge et al. .................... 514/24 |
| 4,652,553 A | 3/1987 | Hagmann et al. ............... 514/26 |
| 4,701,559 A | 10/1987 | Horii et al. ................... 564/363 |
| 4,734,419 A | 3/1988 | Hashimoto et al. ...... 514/266.31 |
| 4,771,050 A | 9/1988 | Meguro et al. ............. 514/224.2 |
| 4,791,126 A | 12/1988 | Tanouchi et al. ............. 514/369 |
| 4,831,045 A | 5/1989 | Tanouchi et al. ............. 514/369 |
| 4,882,315 A | 11/1989 | Chiodini et al. ................ 514/26 |
| 4,883,410 A | 11/1989 | Goddard et al. ............... 417/69 |
| 4,883,800 A | 11/1989 | Hashimoto et al. ...... 514/266.31 |
| 4,931,463 A | 6/1990 | Barbier et al. ............... 514/422 |
| 4,939,140 A | 7/1990 | Larson et al. ............. 514/222.5 |
| 4,980,357 A | 12/1990 | Goldstein et al. ............ 514/278 |
| 5,037,831 A | 8/1991 | Malamas ..................... 514/278 |
| 5,066,659 A | 11/1991 | Lipinski ..................... 514/278 |
| 5,091,418 A | 2/1992 | Sawada et al. ............... 514/569 |
| 5,091,524 A | 2/1992 | Vertesy et al. .............. 536/18.7 |
| 5,157,116 A | 10/1992 | Ducep et al. ................ 536/17.4 |
| 5,175,154 A | 12/1992 | Schwartz et al. ............. 514/172 |
| 5,175,186 A | 12/1992 | Barbier et al. ............... 514/449 |
| 5,192,772 A | 3/1993 | Yoshikuni et al. ............ 514/315 |
| 5,217,877 A | 6/1993 | Sawada et al. ................. 435/64 |
| 5,246,960 A | 9/1993 | Barbier et al. ............... 514/422 |
| 5,252,572 A | 10/1993 | Hermecz et al. .......... 514/259.4 |
| 5,270,342 A | 12/1993 | Brittain et al. ............... 514/617 |
| 5,364,636 A | 11/1994 | Ochi .......................... 424/456 |
| 5,430,060 A | 7/1995 | Brittain et al. ............... 514/617 |
| 5,447,946 A | 9/1995 | Kurono et al. ............... 514/389 |
| 5,504,078 A | 4/1996 | Ducep et al. ................... 514/43 |
| 5,516,516 A | 5/1996 | Cherksey ..................... 424/773 |
| 5,605,698 A | 2/1997 | Ueno .......................... 424/440 |
| 5,693,327 A | 12/1997 | Shah .......................... 424/734 |

(Continued)

FOREIGN PATENT DOCUMENTS

EP    00069439    1/1983

(Continued)

OTHER PUBLICATIONS

Smith, Christo Albertyn "Common Names of South African Plants," Botanical Survey Memoir No. 35 (Ed. E. Percy Phillips, Estelle Van Hoepen) Department of Agricultural Technical Services (Republic of South Africa) 1996 pp. 227, 350, 598, 599.

(Continued)

*Primary Examiner*—Michele Flood
(74) *Attorney, Agent, or Firm*—Morgan, Lewis & Bockius LLP

(57) ABSTRACT

A method of reducing gastric acid secretion in animals including humans comprising administering an extract of a plant of the genus *Hoodia* or *Trichocaulon* to animals, generally mammals.

7 Claims, No Drawings

U.S. PATENT DOCUMENTS

| | | | | |
|---|---|---|---|---|
| 5,698,199 | A | 12/1997 | Mori et al. | 424/734 |
| 5,728,704 | A | 3/1998 | Mylari et al. | 514/256 |
| 5,798,101 | A | 8/1998 | Haveson | 424/730 |
| 5,824,668 | A | 10/1998 | Rubinfeld et al. | 514/170 |
| 5,866,578 | A | 2/1999 | Mylari et al. | 514/256 |
| 5,908,609 | A | 6/1999 | Lee et al. | 424/9.2 |
| 6,100,048 | A | 8/2000 | Cone et al. | 435/7.21 |
| 6,309,853 | B1 | 10/2001 | Friedman et al. | 435/69.1 |
| 6,376,657 | B1 | 4/2002 | Van Heerden et al. | 536/5 |
| 6,488,967 | B1 | 12/2002 | Hakkinen et al. | 424/725 |
| 2002/0146468 | A1 | 10/2002 | Rubin et al. | 424/725 |

FOREIGN PATENT DOCUMENTS

| | | | |
|---|---|---|---|
| EP | 0101383 | A | 2/1984 |
| EP | 0154639 | | 8/1984 |
| EP | 0218953 | | 4/1987 |
| EP | 0219156 | | 4/1987 |
| EP | 0224151 | | 6/1987 |
| EP | 0296574 | | 12/1988 |
| EP | 0749657 | | 12/1996 |
| EP | 0703731 | | 4/1998 |
| EP | 0123456 | | 1/2000 |
| EP | 1099444 | A | 5/2001 |
| FR | 2771105 | | 5/1999 |
| HU | P 99 02670 | A | 2/2000 |
| HU | P 98 03039 | A | 9/2000 |
| JP | 58194818 | | 11/1983 |
| JP | 8332028 | | 12/1996 |
| WO | WO 85 00970 | | 3/1985 |
| WO | WO 90 14827 | | 12/1990 |
| WO | WO 94 24149 | | 10/1994 |
| WO | WO 95 00041 | | 1/1995 |
| WO | WO 95 00161 | | 1/1995 |
| WO | WO 96 39384 | A | 12/1996 |
| WO | WO 96 39385 | A | 12/1996 |
| WO | WO 97 15671 | | 5/1997 |
| WO | WO 97 24369 | A | 7/1997 |
| WO | WO 97 47316 | A | 12/1997 |
| WO | WO 98 10068 | A | 3/1998 |
| WO | WO 98 20121 | | 5/1998 |
| WO | WO 98 27113 | A | 6/1998 |
| WO | WO 98 28335 | A | 7/1998 |
| WO | WO 98 42747 | | 10/1998 |
| WO | WO 98 46243 | A | 10/1998 |

OTHER PUBLICATIONS

Thunberg, Charles Peter, "Travels in Europe, Africa and Asia made between the years 1770 and 1779," vol. 2., F. and C. Rivington 1795, pp. 140, 171.

Pappe, L. "A description of South African forest trees and arborescent shrubs used for technical and economical purposes," 1862 Ward & Co., London, pp. 54-55.

Warburg, Otto, "Die Pflazenwelt, Dritter Band," 1922 Bibliographisches Institut Leipzig (translation of highlighted section attached).

Laidler, P.W. "The magic medicine of the Hottentots" S. Afr. J. Sci. XXV (1928) pp. 433-447.

Marloth, R. "The Flora of South Africa with synopsis of the South African genera of Phanerogamous plants," vol. III, pp. 1000-1002, Wheldon & Wesley, London 1932.

Tschesche, R. et al. "Uber pflanzliche Herzgifte, XXX. Mitteil.: Neue Glykoside aus den Blattern von *Digitalis purpurea* und *Digitalis lanata*" Chemische Berichte 88 (1955) pp. 1569-1576.

J M Watt, MG Breyer-Brandwijk, "The Medicinal and Poisonous Plants of Southern and Eastern Africa," Second Edition, 1962, p. 138.

Heller, M. et al. "Electrophilic Addition to the Δ-14 Double Bond of a Steroid" Steroids 3 (1964) pp. 193-201.

Mitsuhashi, H. et al. "Studies on the Constituents of Asclepiadaceae plants XIII. Epimerization at C-17 and Optical Rotatory Dispersion Study of C/D Cis Pregnane2one Derivatives," Steroids 4 (1964) pp. 483-493.

Tschesche, R. et al. "Uber Digitanolglykoside—IX (1) Zur Konstitution des Digipurpurogenin," Tetrahedron Letters 9 (1964) pp. 473-480.

Borowski, E. et al. "Chemical Studies on Amphotericin B. II. 2-methylheptadecanedioic acid from perhydrogenated amphotericin B," Tetrahedron Letters 9 (1965) pp. 473-478.

Mitsuhashi, H. et al. "Constituents of Asclepiadaceae plants. XVI. Components of *Metaplexis japonica*" Chem. Pharm. Bull. 13 (1965) pp. 1332-1340.

Mitsuhashi, H. et al. "Constituents of Asclepiadaceae plants. XVI. Components of *Metaplexis japonica*" Chemical Abstracts 65 (1966) XP002084116.

Smith, Christo Albertyn "Common Names of South African Plants," Botanical Survey Memoir No. 35 (Ed. E. Percy Phillips, Estelle Van Hoepen) Department of Agricultural Technical Services (Republic of South Africa) 1996 pp. 34-38.

Nikaido, H. et al. "Components of *Boucerosia aucheriana* DECNE," Chem. Pharm. Bull. 15 (1967) pp. 725-726.

Tschesche, R. et al. "Uber Digitanalglykoside, 15. Synthese von 12α20R-Epoxy-5α,14β.17β-H-pregnanen" Chemische Berichte 100 (1967) pp. 464-479.

Oki, M. et al. "Intramolecular interaction between hydroxyl group and carbonyl moiety in keto-alcohols" Bulletin of the Chemical Society of Japan 41 (1968) pp. 176-182.

Hill, BCF "*Hoodia gordonii*," Nat. Cact. and Succ. Journal 24 (1969) pp. 69-70.

Mitsuhashi, H. et al. "Constituents of Asclepiadaceae plants. XXV. Components of *Cynanchum boerhavifolium*" Yagugaku Zasshi 89 (1969) pp. 1352-1357.

Mitsuhashi, H. et al. "Constituents of Asclepiadaceae plants. XXV. Components of *Cynanchum boerhavifolium*," Chemical Abstracts 72 (1970) XP002084115.

Yoshii E. et al. "Preg-14-en-20-ones. Facile preparation and 14β-hydroxylation" Steroids 77 (1972) p. 477.

Bando, H. et al. "Constituents of Asclepiadaceae plants. XXXI. Component of *Stapelia grandiflora*," Chem. Pharm. Bull. 22 (1974) pp. 1209-1211.

Millspaugh, CF "American Medicinal Plants," Dover Publications, Inc., New York (1974) pp. 534-543.

Bruyns, P.V, "Notes on Trichocaulon and Hoodia," Nat. Cact. & Succ. J. 35 (1980) pp. 102-106.

De Rick, A. et al. "Digoxin-quinidine interaction in the dog," J. Vet. Pharmacol. Ther. 43 (1981) pp. 215-218.

Namiki, Shinjuro et al. "Studies on the a-glucoside hydrolase inhibitor, adiposin. I. Isolation and Physicochemical properties," The Journal of Antibiotics 35 (1982) pp. 1234-1236.

Wada et al. "Studies on the constituents of Ascepiadaceae plants. L. Two new oligoglycosides, cynanchoside C2 and cynanchoside CI, from *Cynanchun caudatum* Max.," Chem. Pharm. Sci. 30 (1982) pp. 3500-3504.

Clark, Julia. et al. "The Diabetic Zucker Fatty Rat (41611)," Proceedings of the Society for Experimental Biology and Medicine 173 (1983) pp. 68-75.

Coombes, A.J. "Dictionary of Plants Names," Timber Press Inc., Portland, Oregon (1985) p. 31.

Dolle, R.E. et al. "Total synthesis of elfamycins: aurodox and efrotomycin. 1. Strategy and construction of key intermediates," J. Am. Chem. Soc. 107(1985) pp. 1691-1694.

Dolle, R.E. et al. "Total synthesis of elfamycins: aurodox and efrotomycin. 2. Coupling of key intermediates and completion of the synthesis," J. Am. Chem. Soc. 107 (1985) pp. 1695-1698.

Habermehl, G.G. et al. "Rearrangement of 14β-hydroxy-12β-sulfoxy steroids to 13,17-seco-12,17-cyclosteroids; a 2D-NMR analysis," Z. Naturforsch. 40b (1985) pp. 656-660.

Deepak, D. et al. "A new pregnane glycoside from *Periploca calophylla*," Indian Journal of Chemistry, Section B 25b (1986) pp. 44-45.

Templeton, J.F. et al. "Progesterone Derivatives That Bind to the Digitalis Receptor: Synthesis of 14β-Hydroxyprogesterone. A Novel Steroid with Positive Inotropic Activity," J Med. Chem. B 30 (1987) pp. 1502-1505.

Hayashi, K. et al. "Four pregnane glycosides, boucerosides AI, AII, BI and BII, from *Boucerosia aucheriana*," Phytochemistry 27 (1988) pp. 3919-3924.

Trivedi, R. et al. "A pregnane ester oligoglycoside form *Oxystelma esculentum*," Phytochemistry 28 (1989) pp. 1211-1213.

Foster S, and Duke, J.A. "A Field Guide to Medicinal Plants, Eastern and Central North America," Houghton Mifflin Company, Boston (1990) pp. 136-154.

Johnson, John H. et al. "Underexpression of β Cell High $K_m$ Glucose Transporters in Noninsulin-Dependent Diabetes," Science 250 (1990) pp. 546-549.

Tanaka, T. et al. "Pregnane glycosides from *Boucerosia aucheriana*," Phytochemistry 29 (1990) pp. 229-237.

Chen, J. et al. "A novel $C_{21}$ steroidal glycoside from *Marsdenia incisa*," Yunnan Zhiwu Yanjiu 13 (1991) pp. 231-232 (translation attached as XP002084119, Chemical Abstracts 115 (1991)).

Friedman, Jacob E. "Altered expression of muscle glucose transporter GLUT-4 in diabetic fatty Zucker rats (ZDF/Drt-fα)" Am. J Physiol 261 (Endocrinol. Metab. 24) (1991) pp. E782-E788.

Glendinning, J.I. "Effectiveness of cardenolides as feeding deterrents to Peromyscus mice," Chemical Abstracts 117 (1992) XP002084117.

Glendinning, II. "Effectiveness of cardenolides as feeding deterrents to Peromyscus mice," J Chem. Ecol. 18 (1992) pp. 1559-1575.

Plowes, D.C.H. "A Preliminary Reassessment of the Genera Hoodia and Triehocaulon (Stapelieae: Ascelpiadaceae)," Asklepios 56 (1992) pp. 5-15.

Slieker, L.J. et al. "Glucose transporter levels in tissues of spontaneously diabetic Zucker fa/fa rat (ZDF/drt) and viable yellow mouse (A vy/a)" Diabetes 41 (1992) pp. 187-193.

Bruyns, P. "A Revision of Hoodia and Lavrania (Asceepiadaceae—Stapelieae)," Botanische Jahrbucher fur systematik Pflanzengeschichte and Pflanzengeographie 1152 (1993) pp. 145-270.

Bruyns, P. "New combinations in Hoodia and Lavrania (Ascelpiadaceae—Stapelieae)" South African Journal of Botany 59 (1993) p. 342.

Dohm, G. Lynia, et al. "Acarbose Treatment of Non-Insulin-Dependent Diabetic Fatty (ZDF/Drt-fa) Rats Restores Expression of Skeletal Muscle Glucose Transporter GLUT4," Drugs in Development, vol. 1, α-Glucosidase Inhibition: Potential Use in Diabetes (1993) pp. 173-180.

Milburn, Joseph L., Jr. et al. "β-Cell GLUT-2 Loss and Non-insulin Dependent Diabetes Mellitus: Current Status of the Hypothesis," Diabetes/Metabolism Reviews 9 (1993) pp. 231-236.

Pieber, T.R. et al. "Amylin-insulin relationships in insulin resistance with and without diabetic hyperglycemia" Am J. Physiol. 265 (1993) pp. E446-E453.

Lee, Young et al. "β-Cell lipotoxicity in the pathogenesis of non-insulin-dependent diabetes mellitus of obese rats: Impairment in adipocyte-β-cell relationships," Proc. Natl. Acad. Sci USA 91 (1994) pp. 10878-10882.

Peterson, R.G. "α-Glucosidase inhibitors in diabetes: lessons from animal studies," European Journal of Clinical Investigation 24 Suppl. 3 (1994) pp. 11-18.

Sturis, Jepp et al. "Alterations in pulsatile insulin secretion in the Zucker diabetic fatty rat," Am. J. Physiol. 267 (Endocrinol. Metab. 30) (1994) pp. E250-E259.

Miwa H, et al. "Structural determinants of the melanocortin peptides required for activation of melanocortin-3 and melanocortin-4 receptors," Journal of Pharmacology and Experimental Therapeutics 273 (1995) pp. 367-372.

Ohneda, M. et al. "Caloric restriction in obese pre-diabetic rats prevents beta-cell depletion, loss of beta-cell GLUT 2 and glucose incompetence" Diabetologia 38 (1995) pp. 173-179.

Peterson, Richard G., "The Zucker diabetic fatty (ZDF) rat," Lessons from animal diabetes, V. Ed. E. Shafrir (1995) pp. 225-230.

Chen S.W. et al. "The hyperphagic effect of 3α-hydroxylated pregnane steroids in male rats," Pharmacology Biochemistry and Behaviour 53 (1996) pp. 777-782.

Swarupanandan, K. et al. "The subfamilial and tribal classification of the family Asclepiadaceae," Botanical Journal of the Linnaean Society 1.20 (1996) pp. 327-369.

von Koenen, Eberhard "Heil-, Gift- and eβbare Pflanzen in Namibia," Klaus Hess Verlag (1996) p. 131, (translation of highlighted section attached as entry No. 293).

Yoshikawa, K. et al. "Steroidal glycosides from the fresh stem of *Stephanotis lutchuensis* var. *japonica* (Asclepiadaceae). Chemical structures of stephanosides A-J," Chem. Pharm. Bull. 44 (1996) pp. 1790-1796.

Yoshikawa, K. et al. "Steroidal glycosides from the fresh stem of *Stephanotis lutchuensis* var. *japonica* (Asclepiadaceae). Chemical structures of stephanosides K-Q," Chem. Pharm. Bull. 44 (1996) pp. 2243-2248.

Haskell-Luevano, C, et al. "Discovery of Prototype Peptidomirnetic Agonists at the Human Melanocortin Receptors MC1R and MC4R," J. Med. Chem. 40 (1997) pp. 2133-2139.

Huszar, D. et al. "Targeted Disruption of the Melanocortin-4 Receptor Results in Obesity in Mice" Cell 88 (1997) pp. 131-141.

Fan, W. et al. "Role of melanocortinergic neurons in feeding and the agouti obesity syndrome," Nature 385 (1997) pp. 165-168.

Douketis, J.D. et al. "Periodic health examination, 1999 update: 1. Detection, prevention and treatment of obesity," Canadian Medical Association Journal 160 (1999) pp. 513-525.

Kopelman, P. "Prescribing for obesity," Journal of the Royal College of Physicians of London 33 (1999) pp. 31-32.

Barnett, A. "In Africa, the Hoodia cactus keeps men alive. Now its secret is stolen to make us thin," The Observer Jun. 17, 2001.

Tulp, Orien Lee et al. "Effect of Hoodia Plant on Food Intake and Body Weight in Lean and Obese LA/Ntul//cp Rats," Experimental Biology 2001® Abstracts 2.1-537.42, Part 338.5.

Hargreaves, B. and Queen Turner "Uses and Misuses of Hoodia," Askelpios 86 (2002) pp. 11-16.

"Stomach staples, gastric bypass ops, power-assisted liposuction . . . " The Telegraph, Feb. 14, 2004.

GASTRIC ACID SECRETION

The present application is a continuation application of U.S. patent application Ser. No. 10/171,640 (filed Jun. 17, 2002), now U.S. Pat. No. 6,808,723, which is a divisional application of U.S. patent application Ser. No. 09/691,582 (filed Oct. 18, 2000), now U.S. Pat. No. 6,488,967 which claims the benefit of GB 9925457.5 (filed Oct. 17, 1999) all of which are herein incorporated by reference in their entirety.

This invention relates to the reduction of gastric acid secretion in animals including humans; to methods of treating conditions or disorders associated with or exacerbated by gastric acid secretion; to pharmaceutical compositions useful in carrying out such methods; and to the use of certain extracts and compounds in the treatment of human and non-human animals, generally mammals.

Excessive secretion of gastric acid can lead to or aggravate a number of disorders, for example oesophageal reflux disease, e.g. reflux oesaphagitis, hemorrhage in and benign ulceration of the stomach and duodenum (including those complicating NSAID therapy). These conditions tend to be more problematical in obese patients and patients with hiatus hernia. The present invention is directed, in part, to the treatment of these conditions and of ancillary indications, e.g. to provide relief of reflux-like symptoms (e.g. heartburn) and/or ulcer-like symptoms (e.g. epigastric pain) associated with acid-related dyspepsia; for general dyspeptic symptoms; and for prophylaxis of acid aspiration.

Non-steroidal anti-inflammatory drugs (NSAIDs), e.g. aspirin (acetylsalicylic acid), are well-known and widely used for their anti-inflammatory and antipyretic properties. A major side effect is their tendency to damage the wall of the stomach; this adverse property is acid-dependent and is generic to the NSAIDs. The present invention is also concerned with means for mitigating these adverse effects.

It is known from International Patent Publication No. WO 98/46243 that extracts of certain plants of the genus *Trichocaulon* or *Hoodia* possess appetite suppressant properties. This document also discloses certain specific compounds which possess appetite suppressant activity. Among these is the compound 3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one; the structural formula of this compound is given as formula (1) in WO 98/46243. We have found that this compound is effective in reducing the secretion of gastric acid; accordingly, the compound finds application in the present invention. Derivatives of this compound are also effective in the present invention; such derivatives have the general formula

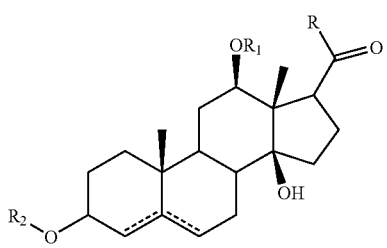

in which
R=alkyl;
$R_1$=H, alkyl, tigloyl, benzoyl, or any other organic ester group;
$R_2$=H, or one or more 6-deoxy carbohydrate, or one or more 2,6-dideoxy carbohydrates, or glucose molecules, or combinations thereof;
in which the acyl group R—(C═O)— group can be in the reduced form R—(C—OH)—;
and in which the dashed lines indicate the optional presence of a double bond in the C4-C5 or C5-C6 positions.

Thus, according to a first aspect of the present invention, there is provided a method of reducing gastric acid secretion in an animal, which comprises administering to said animal:

(a) an extract of a plant of the genus *Hoodia* or *Trichocaulon*; or (b) a compound of the formula

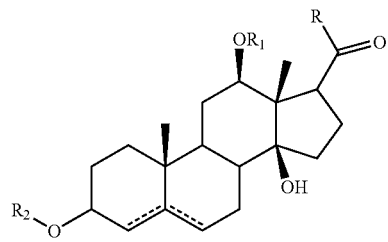

wherein:
R=an alkyl group containing from one to four carbon atoms;
$R_1$=H, an alkyl group containing from one to four carbon atoms, or an organic ester group;
$R_2$=H, or one or more 6-deoxy carbohydrates, or one or more 2,6-dideoxy carbohydrates, or glucose, or a combination thereof;

and in which the dashed bonds indicate the optional presence of a double bond at the C4-C5 position or the C5-C6 position.

Advantageously, when $R_1$ is an organic ester group it is tigloyl, benzoyl or anthraniloyl. In a preferred embodiment, R is an alkyl group having from one to four carbon atoms, $R_1$ is tigloyl or anthraniloyl; and a double bond is present in the C5-C6 position.

Advantageously, $R_2$ is trisaccharide group. The component sugars of said trisaccharide group are preferably 6-deoxy and/or 2,6-dideoxy hexoses. In some embodiments, the terminal hexose moiety is thevetosyl.

The compound may be 3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one.

According to a second aspect of the present invention, there is provided a method of treating a disorder of the alimentary system in an animal, which comprises administering to the animal (a) an extract of a plant of the genus *Hoodia* or *Trichocaulon*; or (b) a compound of the formula

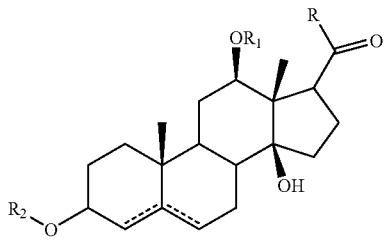

wherein:
R=an alkyl group containing from one to four carbon atoms;
$R_1$=H, an alkyl group containing from one to four carbon atoms, or an organic ester group;
$R_2$=H, or one or more 6-deoxy carbohydrates, or one or more 2,6-dideoxy carbohydrates, or glucose, or a combination thereof;

and in which the dashed bonds indicate the optional presence of a double bond at the C4-C5 position or the C5-C6 position.

This method can conveniently be used in the treatment of reflux oesophagitis. It is also expected to find application in the treatment of epigastric pain; dyspepsia; gastric ulceration; and acid aspiration.

According to a third aspect of the present invention, there is provided a method of protecting a mammalian gastro-intestinal tract from damage caused by a non-steroidal anti-inflammatory drug, which comprises administering an effective amount of:

(a) an extract of a plant of the genus *Hoodia* or *Trichocaulon*; or (b) a compound of the formula

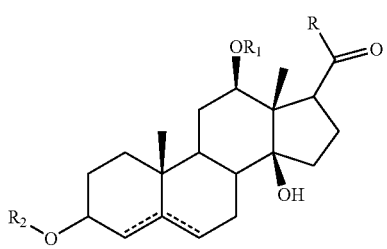

wherein:
R=an alkyl group containing from one to four carbon atoms;
$R_1$=H, an alkyl group containing from one to four carbon atoms, or an organic ester group;
$R_2$=H, or one or more 6-deoxy carbohydrates, or one or more 2,6-dideoxy carbohydrates, or glucose, or a combination thereof;

and in which the dashed bonds indicate the optional presence of a double bond at the C4-C5 position or the C5-C6 position.

According to a fourth aspect, the present invention provides a method of protecting a mammalian gastro-intestinal tract from damage caused by a non-steroidal anti-inflammatory drug, which comprises administering an effective amount of |3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one or a derivative thereof.

When a plant extract is used in the invention, it is presently preferred to use an extract from the plant *Hoodia gordonii* or *Hoodia currori*. Advantageously, the said extract comprises spray-dried sap of the plant *Hoodia gordonii*.

The methods in accordance with this invention are applicable to the treatment of humans.

According to a fifth aspect of the present invention, there is provided a pharmaceutical composition comprising a non-steroidal anti-inflammatory drug and a compound of the formula

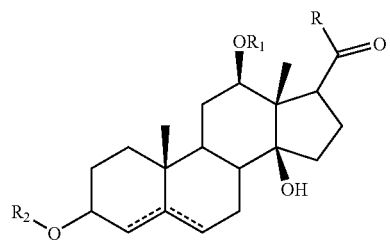

wherein:
R=an alkyl group containing from one to four carbon atoms;
$R_1$=H, an alkyl group containing from one to four carbon atoms, or an organic ester group;
$R_2$=H, or one or more 6-deoxy carbohydrates, or one or more 2,6-dideoxy carbohydrates, or glucose, or a combination thereof;

in which the acyl group R—(C=O)— group can be in the reduced form R—(C—OH)—;

and in which the dashed bonds indicate the optional presence of a double bond at the C4-C5 position or the C5-C6 position.

A preferred pharmaceutical composition of this type utilises the compound 3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one or a derivative thereof. The pharmaceutical compositions of this invention are conveniently prepared in unit dosage form; they may also include a pharmaceutically acceptable diluent, excipient or carrier.

According to a sixth aspect of the present invention, there is provided method of treating a condition or disorder caused by or exacerbated by gastric acid secretion in an animal, which comprises administering to the animal a pharmaceutical composition as just defined. The animal may be a human.

According to a seventh aspect, the present invention provides the use of a compound of the formula

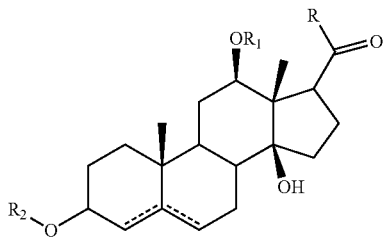

wherein:
- R=an alkyl group containing from one to four carbon atoms;
- $R_1$=H, an alkyl group containing from one to four carbon atoms, or an organic ester group;
- $R_2$=H, or one or more 6-deoxy carbohydrates, or one or more 2,6-dideoxy carbohydrates, or glucose, or a combination thereof;
- in which the acyl group R—(C═O)— group can be in the reduced form R—(C—OH)—;
- and in which the dashed bonds indicate the optional presence of a double bond at the C4-C5 position or the C5-C6 position, in the manufacture of a medicament for the treatment of a disorder caused by or exacerbated by gastric acid secretion. For such use, the compound may be 3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one or a derivative thereof.

According to an eighth aspect, the present invention provides the use of an extract of a plant of the genus *Hoodia* or *Trichocaulon* in the manufacture of a medicament for the treatment of conditions and disorders caused by or exacerbated by gastric acid secretion. The condition or disorder for which the medicament is intended may be reflux oesophagitis; or gastric or duodenal ulceration; gastro-duodenal erosion; or epigastric pain.

According to a ninth aspect, the present invention provides the use of an extract of a plant of the genus *Hoodia* or *Trichocaulon* in the manufacture of a medicament for the treatment of conditions and disorders caused by or exacerbated by gastric acid secretion.

According to a tenth aspect, the present invention provides the use of an extract of a plant of the genus *Hoodia* or *Trichocaulon* in the manufacture of a medicament for the treatment of reflux oesophagitis.

According to an eleventh aspect, the present invention provides the use of an extract of a plant of the genus *Hoodia* or *Trichocaulon* in the manufacture of a medicament for preventing or reducing gastric damage associated with use of a non-steroidal anti-inflammatory drug.

According to a twelfth aspect, the present invention provides the use of 3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one or a derivative thereof in the manufacture of a medicament for preventing or reducing gastric damage associated with use of a non-steroidal anti-inflammatory drug.

The extracts of a plant of the genus *Hoodia* or *Trichocaulon* useful in the present invention may generally be prepared by extracting sap from the plant and then spray-drying the sap. Alternatively, solvent extraction procedures may be employed. In either case, fractionation of the initial extract, e.g. by column chromatography, may follow in order to generate am extract with enhanced activity.

The extract may be prepared from plant material such as the stems and roots of plants of the genus *Hoodia* or the genus *Trichocaulon*; these genera include succulent plants which grow in the arid regions of southern Africa. Advantageously, the plant extract is obtained from one of the following species: *Trichocaulon piliferum*; *Trichocaulon officinale*; *Hoodia currorii*; *Hoodia gordonii*; and *Hoodia lugardii*.

The plant material may be homogenised in the presence of a suitable solvent, e.g. a methanol/methylene chloride solvent, by means of a device such as a Waring blender. The extraction solution may then be separated from residual plant material by an appropriate separation procedure such as, for example, filtration or centrifugation. The solvent may, for example, be removed by means of a rotary evaporator, preferably in a water bath at a temperature of 60° C. The separated crude extract may then be further extracted with methylene chloride and water before being separated into a methylene chloride extract and a water extract. The methylene chloride extract may have the solvent removed by, for example, a rotary evaporator and the resultant extract may be further purified by way of a methanol/hexane extraction. The methanol/hexane extraction product may then be separated to yield a methanol extract and a hexane extract. The methanol extract may be evaporated to remove the solvent in order to yield a partially purified active extract.

The partially purified active extract may be dissolved in methanol, and may be further fractionated by column chromatography, employing silica gel as an adsorption medium and a chloroform/30% methanol mixture as eluent. A plurality of different fractions may be obtained, and each may be evaluated, by suitable bioassaying procedures, to determine their activity. High activity fractions may be further fractionated, e.g. by column chromatography using silica gel as an adsorption medium and a 9:1 chloroform:methanol eluent. This process may be repeated using silica gel as an adsorption medium and a 9:1 ethylacetate:hexane eluent.

Alternatively, the plant product may be compressed or macerated to extract sap therefrom, then filtered to remove unwanted solids and freeze-dried. The freeze-dried sap product may then be further purified, if desired, for example using chromatographic fractionation such as described above.

The derivatives of 3-O-[-β-D-thevetopyranosyl-(1→4)-β-D-cymaropyranosyl-(1→4)-β-D-cymaropyranosyl]-12 β-O-tigloyloxy-14-hydroxy-14β-pregn-5-en-20-one which find use in this invention are advantageously of the formula:

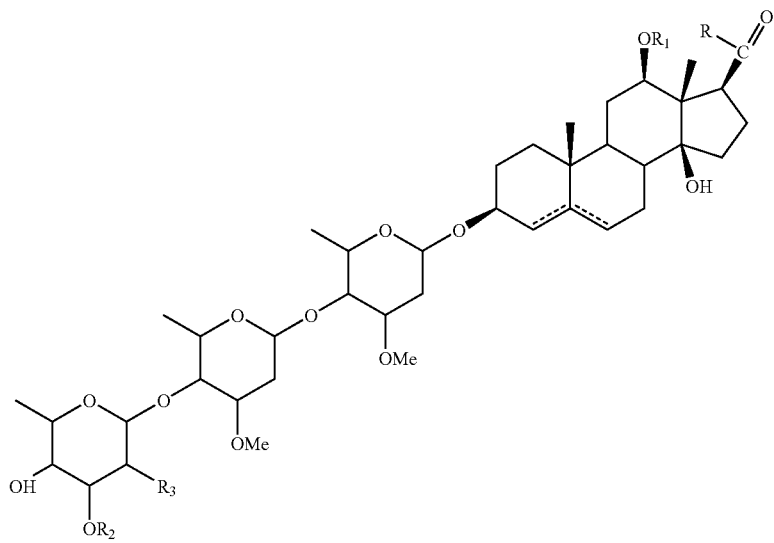

in which
R=alkyl;
R$_1$=H, alkyl, tigloyl, benzoyl, or any other organic ester group;
R$_2$=H or alkyl;
R$_3$=H or OH;
in which the acyl group R—(C═O)— group can be in the reduced form R—(C—OH)—;
and in which the dashed lines indicate the optional presence of a further bond in the C4-C5 or C5-C6 positions;

The invention will be illustrated by the following Examples:

EXAMPLE 1

The ability of the compound 3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one—hereinafter referred to as P57AS3—to prevent aspirin-induced damage to the stomach was investigated in the rat. Three groups each containing eight rats were given aspirin in 0.5% CMC orally at a dose of about 600 mg/kg (1.0 ml of 60 mg/ml). The first group (the control group) was additionally given 0.5% CMC. The second group was given compound P57AS3 at a dose rate of 100 mg/kg; and the third group (comparative group) was given cimetidine at a dose rate of 20 mg/kg.

After 5 hours, the animals' stomachs were visually inspected for damage. Damage was assessed on a scale in which each small haemorrhage scored one point; each large haemorrhage scored two points; each small ulcer scored three points; and each large ulcer scored four points. The results obtained were as follows:

TABLE 1

| Oral treatment | Dose (mg/kg) | Rat no. | Gastric damage score |
|---|---|---|---|
| Vehicle (0.5% CMC) | — | 1 | 10 |
| | | 2 | 10 |
| | | 3 | 16 |
| | | 4 | 8 |

TABLE 1-continued

| Oral treatment | Dose (mg/kg) | Rat no. | Gastric damage score |
|---|---|---|---|
| | | 5 | 5 |
| | | 6 | 3 |
| | | 7 | 1 |
| | | 8 | 6 |
| | | Mean | 7.38 |
| P57AS3 | 100 | 9 | 0 |
| | | 10 | 0 |
| | | 11 | 3 |
| | | 12 | 0 |
| | | 13 | 0 |
| | | 14 | 0 |
| | | 15 | 2 |
| | | 16 | 0 |
| | | Mean | 0.63 |
| Cimetidine | 20 | 17 | 0 |
| | | 18 | 0 |
| | | 19 | 4 |
| | | 20 | 0 |
| | | 21 | 0 |
| | | 22 | 0 |
| | | 23 | 0 |
| | | 24 | 0 |
| | | Mean | 0.50 |

These results show that compound P57AS3 gave an average reduction in gastric damage of 91.5% compared to 93.2% for cimetidine. In both cases, the statistical significance of the difference from the control group was P<0.01.

EXAMPLE 2

The effect of both the spray dried extract (sap from *Hoodia gordonii*)—referred to hereinafter as P57SD—and the purified compound P57AS3 were examined for effects on gastric acid secretion in the pylorus-ligated rat. Male Sprague-Dawley derived CD rats, 175-230 g, were used. On the day before the test, rats were outfitted with stainless steel tail cups to prevent coprophagy, housed individually with water allowed ad lib, and fasted overnight (18 hr). In one test the spray dried sap P57SD (5 or 50 mg/kg), or cimetidine (10 mg/kg) or vehicle (water) was orally administered to the rats immediately before fasting. Water was removed 30 minutes prior to ligation on the morning of the test. Under isoflurane anethesia; a midline celiotomy was performed, and the pylorus of each rat was ligated with 4-0 silk.

In a second experiment, purified compound P57AS3 was administered intraduodenally (i.d.) at 1 or 10 mg/kg at the time of the pylorus ligation. In this experiment with intraduodenal administration of P57AS3, vehicle (DMSO), cimetidine (10 mg/kg) or P57AS3 (1 or 10 mg/kg) was administered immediately after ligation. The incisions were then closed with staples. In the experiments with subcutaneous administration of P57, vehicle (DMSO), cimetidine (10 mg/kg) or P57, 10 or 30 mg/kg were injected subcutaneously in the nape of the neck immediately after the incisions were closed. Two hours after ligation, the rats were killed, the contents of each stomach collected and cleaned by centrifugation (30 minutes at 2000×g), and the volume of gastric fluid in each stomach was determined. Using a Radiometer pH meter and autotitrator, the pH and acid concentration of each gastric sample was determined by titration to pH 7 with 0.1N NaOH. Results are expressed as µeq/hr/100 g (body weight) and % vehicle control.

In the first experiment, gastric acid output was determined 18 hours after rats were orally administered the spray dried sap P57SD. Results showed that the 5 mg/kg dose of P57SD was without effect, but the 50 mg/kg dose-inhibited gastric acid secretion by 40% (Table 2). In a second experiment, the purified compound P57AS3 was administered intraduodenally (i.d.) at 1 or 10 mg/kg at the time of the pylorus ligation. The 10 mg/kg i.d. dose of P57AS3 decreased acid secretion by 88%, but the 1 mg/kg i.d. dose had no effect (Table 2). Experiments were then conducted to determine if systemically administered P57AS3 would also inhibit gastric acid secretion. P57AS3 was administered subcutaneously at the time of ligation in 3 experiments using 10 mg/kg and in one experiment using 30 mg/kg. In one of the experiments with 10 mg/kg, P57AS3 produced a significant decrease in gastric acid secretion, but in the other 2 experiments with 10 mg/kg and the one experiment with 30 mg/kg there was a trend toward decreased acid output but the amount of acid secretion was not significantly different from vehicle-treated controls (Table 2). In each pylorus ligation experiment, gastric acid secretion was significantly reduced (range 36% to 83% inhibition) in a group of rats treated with cimetidine (10 mg/kg), which was included as a positive control.

TABLE 2

Effect of P57 on gastric acid secretion in the pylorus-ligated rat

| Exp. | Active | Dose (mg/kg) | Route Acid Output | % Control mean ± sd |
|---|---|---|---|---|
| I | P57SD | 5 | po | 85.4 ± 34.5 |
|   |       | 50 | po | *60.0 ± 21.7 |
| II | P57AS3 | 1 | id | 109.0 ± 37.8 |
|    |        | 10 | id | *12.4 ± 1.1 |
| III | P57AS3 | 10 | sc | 48.9 ± 29.2 |
| IV | P57AS3 | 10 | sc | 74.0 ± 38.0 |
| V | P57AS3 | 10 | sc | *57.1 ± 19.8 |
| VI | P57AS3 | 30 | sc | 63.7 ± 17.3 |

*significantly different from vehicle group, $p \leq 0.05$

SUMMARY OF RESULTS

In Vitro Studies

Purified P57AS3 was examined for binding affinity to a variety of receptors, channels, and uptake sites in vitro. At a concentration of 10 µM, In isolated tissue studies, P57AS3 at concentrations $\leq 10$ µM had no effect on the rate of spontaneously beating guinea pig right atria or on the force of contraction of electrically stimulated left atria. At concentrations of 1 µM and higher, P57AS3 produced intermittent and transient elevations in the basal tension of electrically stimulated left atria. P57AS3 had no effect on resting tension of isolated guinea pig gallbladder, ileum or trachea, or on CCK octapeptide-induced contractions of the gallbladder (CCK-A receptor mediated), histamine induced contractions of the guinea pig ileum ($H_1$ receptor mediated), or acetylcholine-induced contractions of the guinea pig ileum ($M_3$ receptor mediated). At concentrations $\geq 1$ µM, P57AS3 noncompetitively inhibited carbachol-induced contractions of the guinea pig trachea ($M_3$ receptor mediated).

In Vivo Studies

The spray dried form of P57 was examined for effects on gastrointestinal motility and both the spray dried and purified forms were examined for effects on gastric acid secretion in the rat. At a dose of 5 mg/kg p.o., spray dried P57 had no effect on gastrointestinal transit or on gastric acid secretion. However, a 50 mg/kg dose of spray dried P57 inhibited gastric emptying by 26% and acid output by 40%. Following intraduodenal (id) administration in the rat, purified P57AS3 had no effect on gastric acid secretion at a dose of 1 mg/kg, but a 10 mg/kg dose decreased acid output by 88%. In 2 of 3 experiments at a dose of 10 mg/kg and in one experiment at a dose of 30 mg/kg, subcutaneously (sc) administered purified P57AS3 had no effect on gastric acid output, but in 1 of 3 experiments the 10 mg/kg sc dose reduced gastric acid secretion by 43%.

REFERENCES

1. Hill S J, and Young J M. Characterization of [3H]mepyramine binding to the longitudinal muscle of guinea pig small intestine. Mol Pharmacol 1981; 19:379-387
2. Eltze M, Mutschler E, and Lambrecht G. Affinity profiles of pizotifen, ketotifen and other tricyclic antimuscarinics at muscarinic receptor subtypes $M_1$, $M_2$ and $M_3$. Eur J Pharmacol 1992; 211:283-293.
3. Bishop L A, Gerskowitch V P, Hull R A, Shankley N P, Black J W. Combined dose-ratio analysis of cholecystokinin receptor antagonists, devazepide, lorglumide and loxiglumide in the guinea pig gallbladder. Br J Pharmacol 1992; 106:61-66.

The invention claimed is:

1. A method of reducing gastric acid secretion in an animal, comprising administering to said animal in need thereof an effective amount of either:

(a) an extract of a plant of the genus *Hoodia* or *Trichocaulon*; or
(b) a compound of the formula

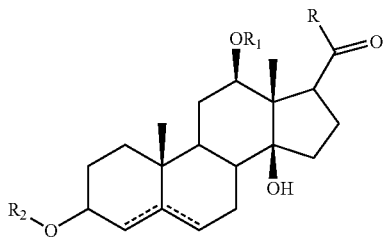

wherein:
R=an alkyl group containing from one to four carbon atoms;
$R_1$=H, an alkyl group containing from one to four carbon atoms, or an organic ester group;
$R_2$=H, or one or more 6-deoxy carbohydrates, or one or more 2,6-dideoxy carbohydrates, or glucose, or a combination thereof;

and in which the dashed bonds indicate the optional presence of a double bond at the C4-C5 position or the C5-C6 position.

2. The method according to claim 1, wherein said organic ester group is tigloyl or benzoyl or anthraniloyl.

3. The method according to claim 1, wherein
R is an alkyl group having from one to four carbon atoms,
$R_1$ is tigloyl or anthraniloyl;
and a double bond is present in the C5-C6 position.

4. The method according to claim 1, wherein $R_2$ is a trisaccharide group.

5. The method according to claim 4, wherein component sugars of said trisaccharide group are 6-deoxy and/or 2,6-dideoxy hexoses.

6. The method according to claim 5, wherein a hexose thevetosyl is at the terminus of the trisaccharide group.

7. The method according to claim 1, wherein the compound is 3-O-[β-D-thevetopyranosyl -(1→4)-β-D-cymaropyranosyl-(1→4)-β-D-cymaropyranosyl]-12β-O-tigloyloxy -14-hydroxy- 14β-pregn-5-en-20-one.

* * * * *